United States Patent
Ito et al.

(10) Patent No.: US 10,532,879 B2
(45) Date of Patent: Jan. 14, 2020

(54) DISPENSER AND SHIELD

(71) Applicant: 3M INNOVATIVE PROPERTIES COMPANY, Saint Paul, MN (US)

(72) Inventors: Tomomi Ito, Sagamihara (JP); Shingo Kawasaki, Kanagawa (JP); Yo Suzuki, Tokyo (JP); Naoto Uchida, Tokyo (JP)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 15/767,072

(22) PCT Filed: Oct. 13, 2016

(86) PCT No.: PCT/US2016/056736
§ 371 (c)(1),
(2) Date: Apr. 9, 2018

(87) PCT Pub. No.: WO2017/066380
PCT Pub. Date: Apr. 20, 2017

(65) Prior Publication Data
US 2019/0062039 A1    Feb. 28, 2019

(30) Foreign Application Priority Data
Oct. 15, 2015 (JP) .................. 2015-203762

(51) Int. Cl.
*B65D 83/08* (2006.01)
*A62B 18/08* (2006.01)
(Continued)

(52) U.S. Cl.
CPC .......... *B65D 83/0805* (2013.01); *A61F 9/045* (2013.01); *A62B 18/082* (2013.01); *A62B 23/025* (2013.01)

(58) Field of Classification Search
USPC ...... 206/499, 438, 820; 128/205.25, 201.17; 221/33, 34, 303, 45, 309; 2/9
See application file for complete search history.

(56) References Cited

U.S. PATENT DOCUMENTS 3,261,027 A * 7/1966 Lambert ................ A45D 44/12
128/857
4,269,315 A    5/1981 Boyce
(Continued)

FOREIGN PATENT DOCUMENTS

EP    1147996    10/2001
JP    07149380    6/1995
(Continued)

OTHER PUBLICATIONS

International Search Report for PCT International Application No. PCT/US2016/056736, dated Jan. 25, 2017, 4 pages.
(Continued)

*Primary Examiner* — Jacob K Ackun
(74) *Attorney, Agent, or Firm* — 3M Innovative Properties Company; Trisha D. Adamson

(57) ABSTRACT

To provide a shield and a dispenser from which the shield can be easily dispensed, the dispenser (100) according to the present invention stores a plurality of shields (1A) in a mutually detachable joined state in the container (50). As such, sliding and the like of the plurality of the shields (1A) against each other in the container (50) is suppressed and, therefore, sticking of the shields (1A) to each other due to the generation of static electricity is suppressed. Thus, a user can easily dispense the shields (1A) from the dispensing opening (51) of the container (50).

5 Claims, 14 Drawing Sheets

(51) Int. Cl.
  *A62B 23/02* (2006.01)
  *A61F 9/04* (2006.01)

(56) References Cited

U.S. PATENT DOCUMENTS

| | | | |
|---|---|---|---|
| 4,673,084 A | 6/1987 | Hubbard | |
| 4,674,634 A * | 6/1987 | Wilson | B65D 33/001 206/494 |
| 4,768,810 A * | 9/1988 | Mertens | B41L 1/26 281/5 |
| 4,852,185 A * | 8/1989 | Olson | A61F 9/02 2/9 |
| 4,856,535 A * | 8/1989 | Forbes | A41D 13/1176 128/857 |
| 5,050,909 A * | 9/1991 | Mertens | B41L 1/24 281/15.1 |
| 5,080,254 A * | 1/1992 | Feer | B42D 5/005 206/215 |
| 5,303,423 A * | 4/1994 | Gazzara | A61F 9/02 128/857 |
| 5,406,944 A * | 4/1995 | Gazzara | A41D 13/1184 128/201.12 |
| 5,520,308 A * | 5/1996 | Berg, Jr. | B65D 83/0894 221/50 |
| 5,584,078 A * | 12/1996 | Saboory | A41D 13/1184 128/201.17 |
| 5,615,767 A | 4/1997 | Eull | |
| 5,881,877 A * | 3/1999 | Adams | A45C 11/04 206/373 |
| 6,026,511 A | 2/2000 | Baumann | |
| 6,238,510 B1 | 5/2001 | Callahan, Jr. | |
| 6,286,712 B1 * | 9/2001 | Craig | B65H 45/24 206/494 |
| 6,694,971 B2 | 2/2004 | Schroeder | |
| 7,032,751 B2 * | 4/2006 | Bell | A41D 13/1161 128/206.19 |
| 7,811,649 B2 * | 10/2010 | Post | A47L 13/20 206/820 |
| 8,967,427 B2 * | 3/2015 | Hogan | B65D 83/0847 221/309 |
| 2001/0007325 A1 * | 7/2001 | Kroll et al. | A47G 19/10 220/574 |
| 2007/0062843 A1 * | 3/2007 | Rudd | B65D 83/0805 206/581 |
| 2007/0205212 A1 * | 9/2007 | Klingel | B65H 37/04 221/33 |
| 2007/0210096 A1 * | 9/2007 | Ellswood | B65D 5/542 221/34 |
| 2008/0066209 A1 * | 3/2008 | Kayerod | A45D 44/12 2/15 |
| 2009/0050646 A1 * | 2/2009 | Windorski | B42D 5/005 221/33 |
| 2009/0188015 A1 * | 7/2009 | Grad | A61F 9/025 2/15 |
| 2012/0325843 A1 * | 12/2012 | Tsuei | A62B 23/025 221/303 |
| 2015/0102050 A1 * | 4/2015 | Marin-Quintero | B65D 75/5838 221/63 |
| 2015/0266655 A1 | 9/2015 | Duffy | |
| 2015/0351965 A1 * | 12/2015 | Umentum | A61F 9/04 221/92 |
| 2016/0060019 A1 * | 3/2016 | Ishihara | B65D 75/5838 206/205 |

FOREIGN PATENT DOCUMENTS

| | | |
|---|---|---|
| JP | 09220120 | 8/1997 |
| JP | 2001525203 | 12/2001 |
| JP | 3372692 | 2/2003 |
| JP | 2003521427 | 7/2003 |
| JP | 2007254023 | 10/2007 |
| JP | 4216575 | 1/2009 |
| JP | 4500835 | 7/2010 |
| JP | 2012504012 | 2/2012 |
| JP | 2012158380 | 8/2012 |
| JP | 5049698 | 10/2012 |
| JP | 5134801 | 1/2013 |
| JP | 2013151308 | 8/2013 |
| JP | 2014500201 | 1/2014 |
| JP | 1515180 | 1/2015 |
| JP | 1515181 | 1/2015 |
| JP | 2015142654 | 8/2015 |
| WO | WO 2009-004921 | 1/2009 |
| WO | WO 2015-116579 | 8/2015 |

OTHER PUBLICATIONS

Supplementary European Search Report for Application No. EP 16856146, dated Mar. 25, 2019.

* cited by examiner

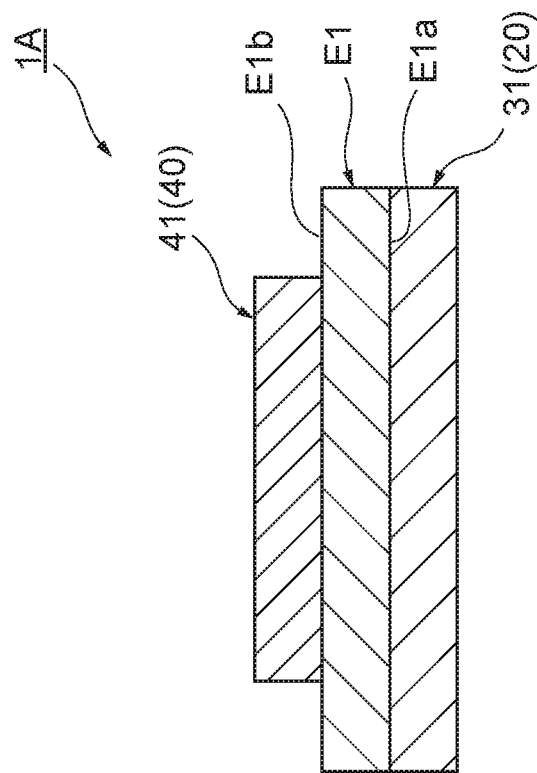
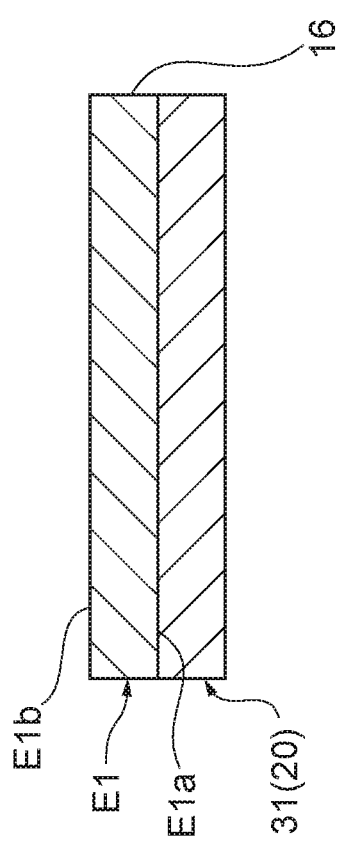
Fig. 4

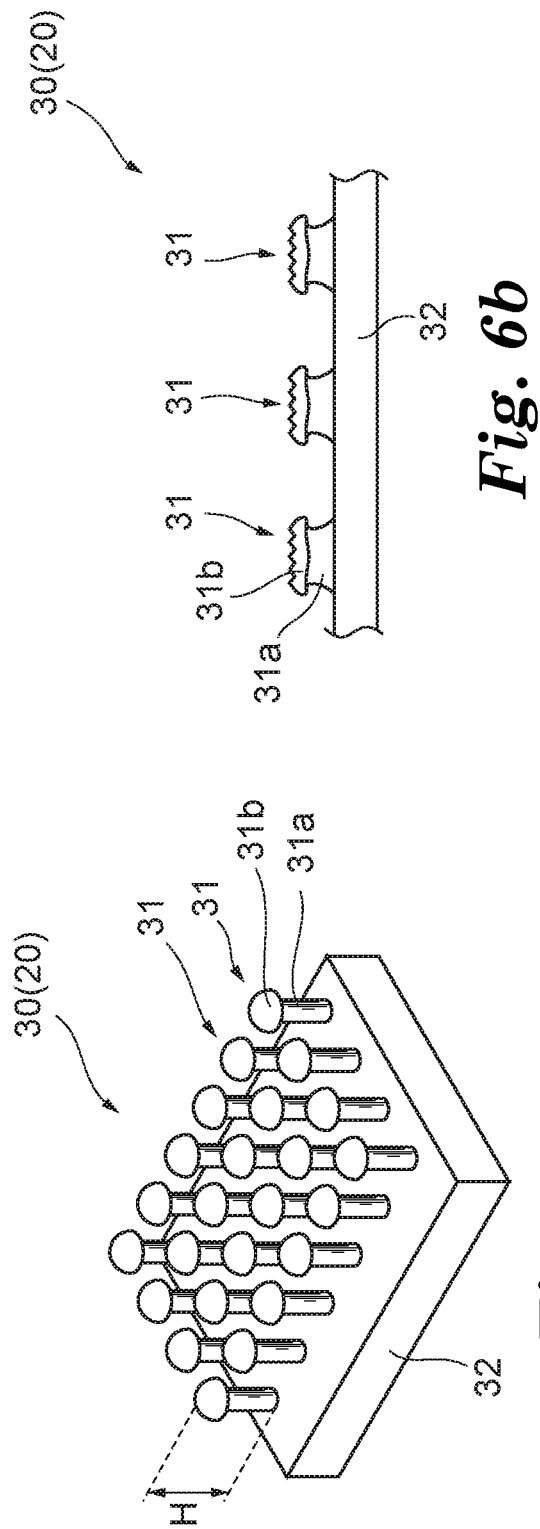
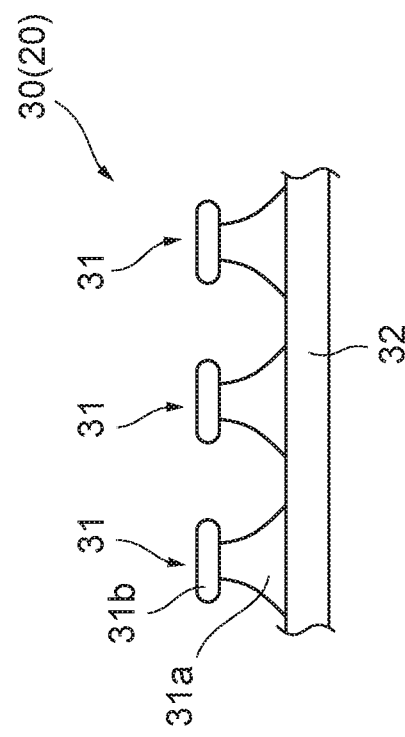

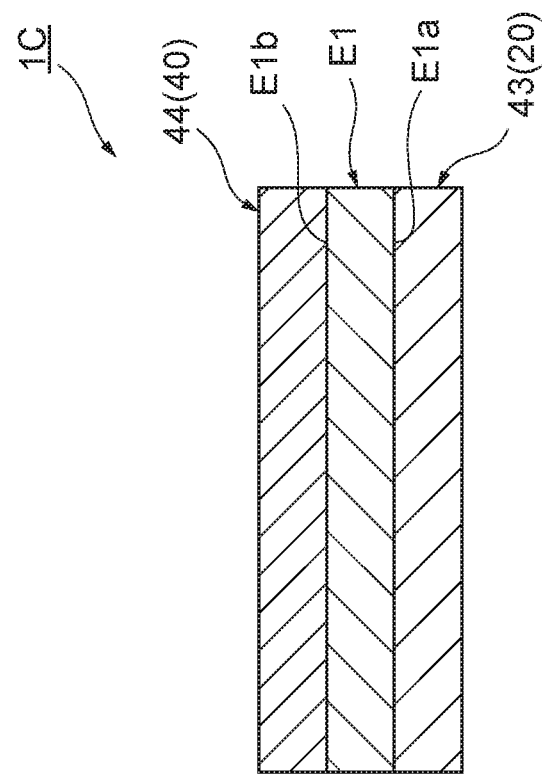
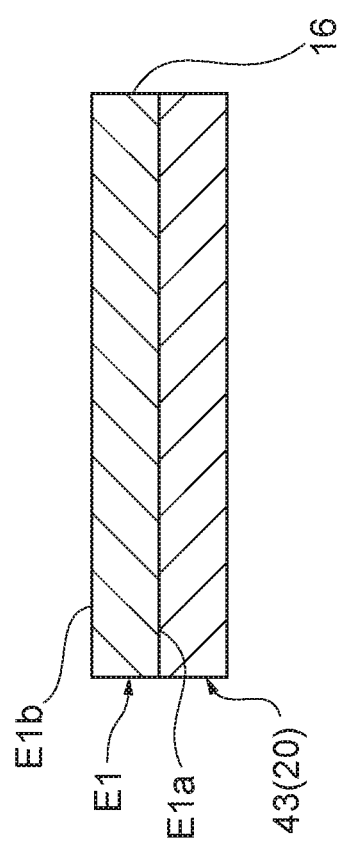
Fig. 11

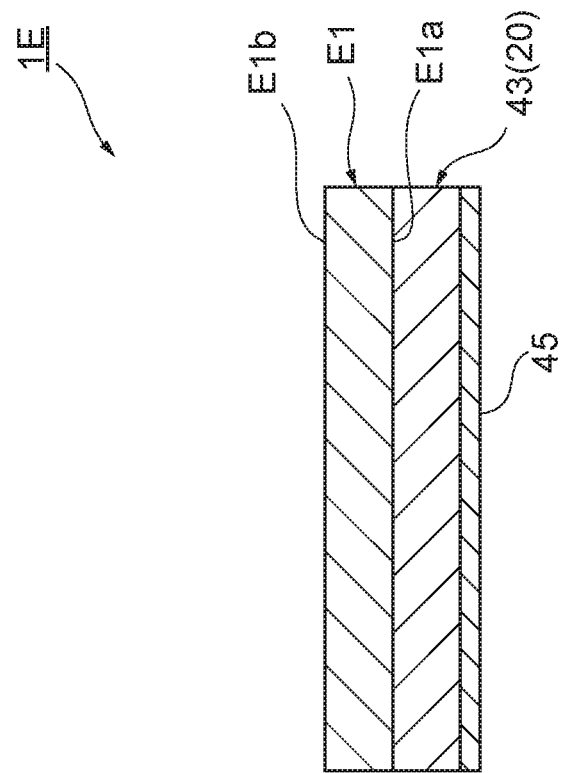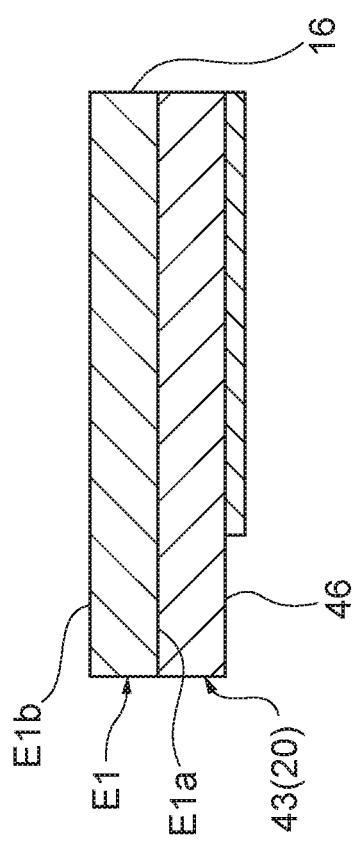
Fig. 13

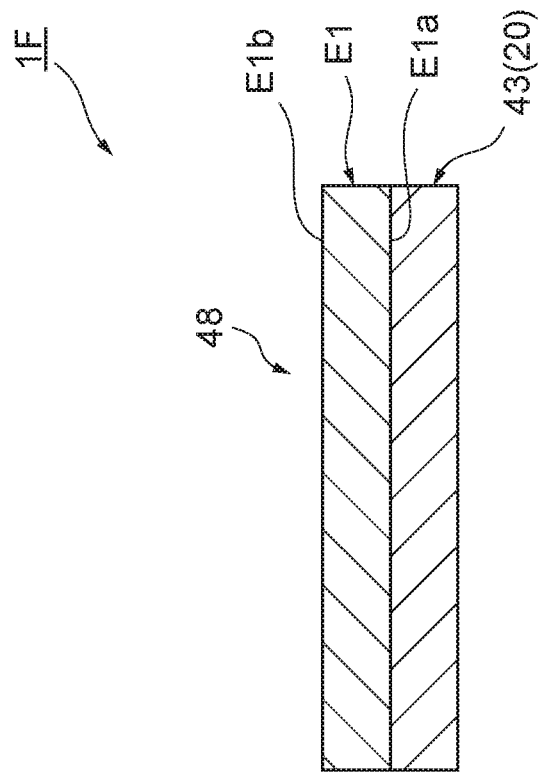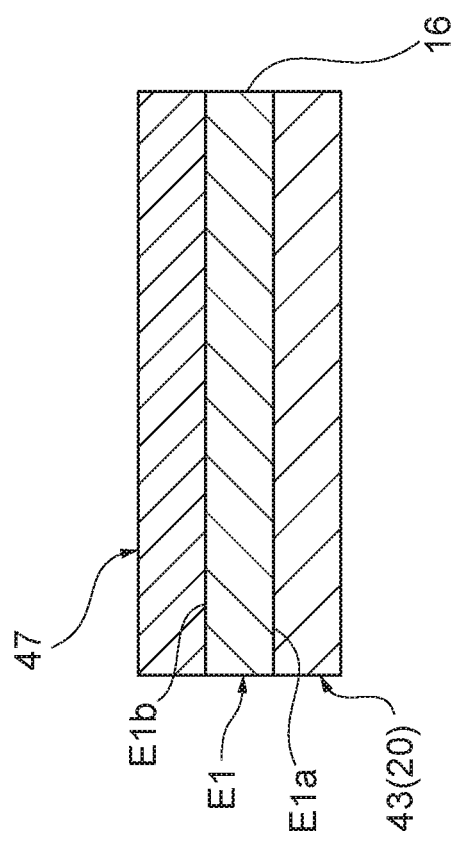
Fig. 14

DISPENSER AND SHIELD

CROSS REFERENCE TO RELATED APPLICATIONS

This application is a national stage filing under 35 U.S.C. 371 of International Application No. PCT/US2016/056736, filed Oct. 13, 2016, which claims the benefit of Japanese Application No. 2015-203762, filed Oct. 16, 2015. The disclosures of both applications are incorporated by reference in their entirety herein.

TECHNICAL FIELD

An aspect of the present invention relates to a shield and a dispenser of shields used in masks.

BACKGROUND

Conventionally, shields are known that protect the eyes of a user wearing a non-woven mask. For example, Japanese Unexamined Patent Application No. 2015-142654A describes a shield provided with an attachment section that overlaps with a non-woven mask and attaches to the non-woven mask, and an eye protection section capable of protecting the eyes of a user.

SUMMARY

A plurality of the shields described above is stored in a container in a stacked state. Consequently, the shields may slide against each other in the container, resulting in the generation of static electricity. In such a case, the shields stick to each other due to the generation of static electricity and, therefore, it is difficult to dispense the shields one at a time without touching the other shields. Thus, in the present technical field, there is a need for a shield and a dispenser from which shields can be easily dispensed.

A dispenser according to one aspect of the present invention includes a shield configured to protect eyes of a user wearing a non-woven mask, and a container configured to store a stacked body constituted by a plurality of shields stacked in a mutually detachable joined state. In such a dispenser, the container includes dispensing means through which the shields can pass.

With this dispenser, the plurality of shields are stored in a mutually detachable joined state in the container. As such, sliding and the like of the plurality of shields against each other in the container is suppressed and, therefore, sticking of the shields to each other due to the generation of static electricity is suppressed. Thus, the user can easily dispense the shields from the dispensing means of the container.

Additionally, with a dispenser according to another aspect, the stacked body may include at least a first shield, a second shield, and a third shield stacked in this order toward one direction of a stacking direction. The first shield and the second shield may be mutually detachably joined at a first joining section positioned in a region on a first side in a width direction of the shields. The second shield and the third shield may be mutually detachably joined at a second joining section positioned in a region on a side opposite the first side in the width direction, namely a second side, of the shields. The container may include dispensing means located between positions, each covering the first joining section and the second joining section in the stacking direction in a state in which the stacked body is stored. In this case, for example, in a case where an uppermost shield of the stacked body is the third shield, first, the region on the side opposite the second joining section in the width direction of the third shield is in a state protruding out from the dispensing means of the container. Then, when the user grabs and pulls the third shield, the region on the second joining section side in the width direction of the third shield is pulled out and, at the same time, the second shield follows via the second joining section and is pulled out. As a result, the region on the second joining section side in the width direction of the second shield (that is, the region on the side opposite the first joining section) assumes a state protruding out from the dispensing means of the container. Then, likewise, when the user grabs and pulls the second shield, the region on the first joining section side in the width direction of the second shield is pulled out and, at the same time, the first shield follows via the first joining section and is pulled out. As a result, the region on the first joining section side in the width direction of the first shield assumes a state protruding out from the dispensing means of the container. According to this dispenser, by continuing and repeating the same operations, the shields can be easily dispensed without touching the other shields.

Additionally, in a dispenser according to another aspect, the shield may include an attachment section that is formed on a lower edge section side of the shield, overlaps with the non-woven mask, and attaches to the non-woven mask. In the attachment section, a connecting portion detachably securing to the non-woven mask may be formed in substantially all regions in the width direction of the shield, on a surface side, namely a back surface side, where the shield overlaps with the non-woven mask. In this case, because the connecting portion is formed on the lower edge section side of the shield, an excellent field of view of the user can be ensured while using the shield. Additionally, because the connecting portion is formed in substantially all regions in the width direction of the shield, it is possible to reliably detachably secure the shield to the non-woven mask.

Additionally, in a dispenser according to another aspect, the first joining section and the second joining section may be constituted by the connecting portion that is formed by mechanical engagement means including male engagement elements, and joining means that are provided on a front surface side of the attachment section and that detachably join with the mechanical engagement means. In this case, because the connecting portion is formed by the mechanical engagement means including the male engagement elements, connecting strength will not easily decline, even when the shield is repeatedly attached to and detached from the non-woven mask. Additionally, because the mechanical engagement means do not function only as the connecting portion, but also function as a portion of the first joining section and the second joining section, the configuration of the shield can be simplified.

Additionally, in a dispenser according to another aspect, the first joining section and the second joining section may be constituted by the connecting portion that includes a first adhesive, and a second adhesive that is provided on the front surface side of the attachment section. In this case, adhesive strength between a region on the front surface side of the attachment section where the second adhesive is provided and the connecting portion that includes the first adhesive is stronger than adhesive strength between a region on the front surface side of the attachment section where the second adhesive is not provided and the connecting portion that includes the first adhesive. Due to this difference in adhesive strengths, the region on the front surface side of the attachment section where the second adhesive is provided and the connecting portion that includes the first adhesive function as the first joining section and the second joining section. Here, because the adhesives can be formed thinly, increases in the thicknesses of the first joining section and the second joining section can be suppressed.

Additionally, in a dispenser according to another aspect, the shield may further include a liner covering an entire surface of the first adhesive on the surface side that overlaps with the non-woven mask. In this case, the first joining section and the second joining section are constituted by the second adhesive and, because the adhesive can be formed thinly, increases in the thicknesses of the first joining section and the second joining section can be suppressed.

Additionally, in a dispenser according to another aspect, the first joining section and the second joining section may be constituted by an exposed portion, that is, a remaining portion where the connecting portion that includes the first adhesive is exposed from the liner that covers a portion of the surface side that overlaps with the non-woven mask; and a portion on the front surface side of the attachment section. In this case, the first joining section and the second joining section are constituted by the exposed portion where the first adhesive is exposed from the liner. Additionally, because the adhesive can be formed thinly, increases in the thicknesses of the first joining section and the second joining section can be suppressed. Additionally, because the first adhesive does not function only as the connecting portion, but also functions as the first joining section and the second joining section, the configuration of the shield can be simplified.

Additionally, in a dispenser according to another aspect, the first joining section and the second joining section may be constituted by the connecting portion that includes a first adhesive; and an exposed portion, that is, a remaining portion that is not covered by an easy-release layer, of the front surface side of the attachment section of which a portion is covered by the easy-release layer on a surface side of a side opposite a surface that overlaps with the non-woven mask.

In this case, adhesive strength between the remaining portion, namely the exposed portion, and the connecting portion that includes the first adhesive is stronger than adhesive strength between the easy-release layer and the connecting portion that includes the first adhesive. Due to this difference in adhesive strengths, the remaining portion, namely the exposed portion, and the connecting portion that includes the first adhesive function as the first joining section and the second joining section. Here, because the adhesive can be formed thinly, increases in the thicknesses of the first joining section and the second joining section can be suppressed.

Additionally, a shield according to an aspect of the present invention is a shield configured to protect the eyes of a user wearing a non-woven mask. The shield is provided with an attachment section that is formed on a lower edge section side of the shield, overlaps with the non-woven mask, and attaches to the non-woven mask and an eye protection section that is formed on an upper edge section side of the shield and is capable of protecting the eyes of a user. In the attachment section, a connecting portion detachably securing to the non-woven mask and formed by mechanical engagement means including male engagement elements is formed in substantially all regions in the width direction of the shield. Additionally, joining means that detachably join with the mechanical engagement means are provided on the front surface side of the attachment section, in a region on a first side in the width direction of the shield.

In cases where a plurality of the shield exists, it is possible to mutually detachably join these shields via the connecting portion and the joining means. Accordingly, when stored in a container in a state where the plurality of shields are detachably joined, sliding and the like of the plurality of shields against each other in the container is suppressed and, therefore, sticking of the shields to each other due to the generation of static electricity is suppressed. Thus, the user can easily dispense the shields out of the container. Additionally, the joining means are provided only in the region on the first side in the width direction of the shield. As such, for example, in a case where two of the shields are mutually detachably joined via the connecting portion and the joining means and stored in the container that includes the dispensing means described above, first, a region on a side opposite the first side in the width direction of the upper shield where the joining means are provided is in a state protruding out from the dispensing means of the container. Then, when the user grabs and pulls the upper shield, the region on the first side in the width direction of the upper shield where the joining means are provided is pulled out and, at the same time, the lower shield follows via the connecting portion and the joining section of the joining means and is pulled out. As a result, the region on the first side in the width direction of the lower shield where the joining means are provided assumes a state protruding out from the dispensing means of the container. Thus, according to this shield, the shields can be easily dispensed without touching the other shields. Additionally, because the connecting portion is constituted by the mechanical engagement means including male engagement elements, compared to a case where the connecting portion includes an adhesive, even if the shield unintentionally comes in contact with other members when using, joining will not occur and, thus, handling is simple.

According to one aspect of the present invention, shields can easily be dispensed.

BRIEF DESCRIPTION OF DRAWINGS

FIG. 4 is a drawing schematically illustrating a cross-section taken along a line IV-IV of the shield depicted in FIG. 3A.

FIGS. 6A to 6C are drawings illustrating examples of the mechanical engagement means.

FIG. 11 is a drawing schematically illustrating a cross-section of a shield according to a third embodiment.

FIG. 13 is a drawing schematically illustrating a cross-section of a shield according to a fifth embodiment.

FIG. 14 is a drawing schematically illustrating a cross-section of a shield according to a sixth embodiment.

DESCRIPTION OF EMBODIMENTS

Figure 1:
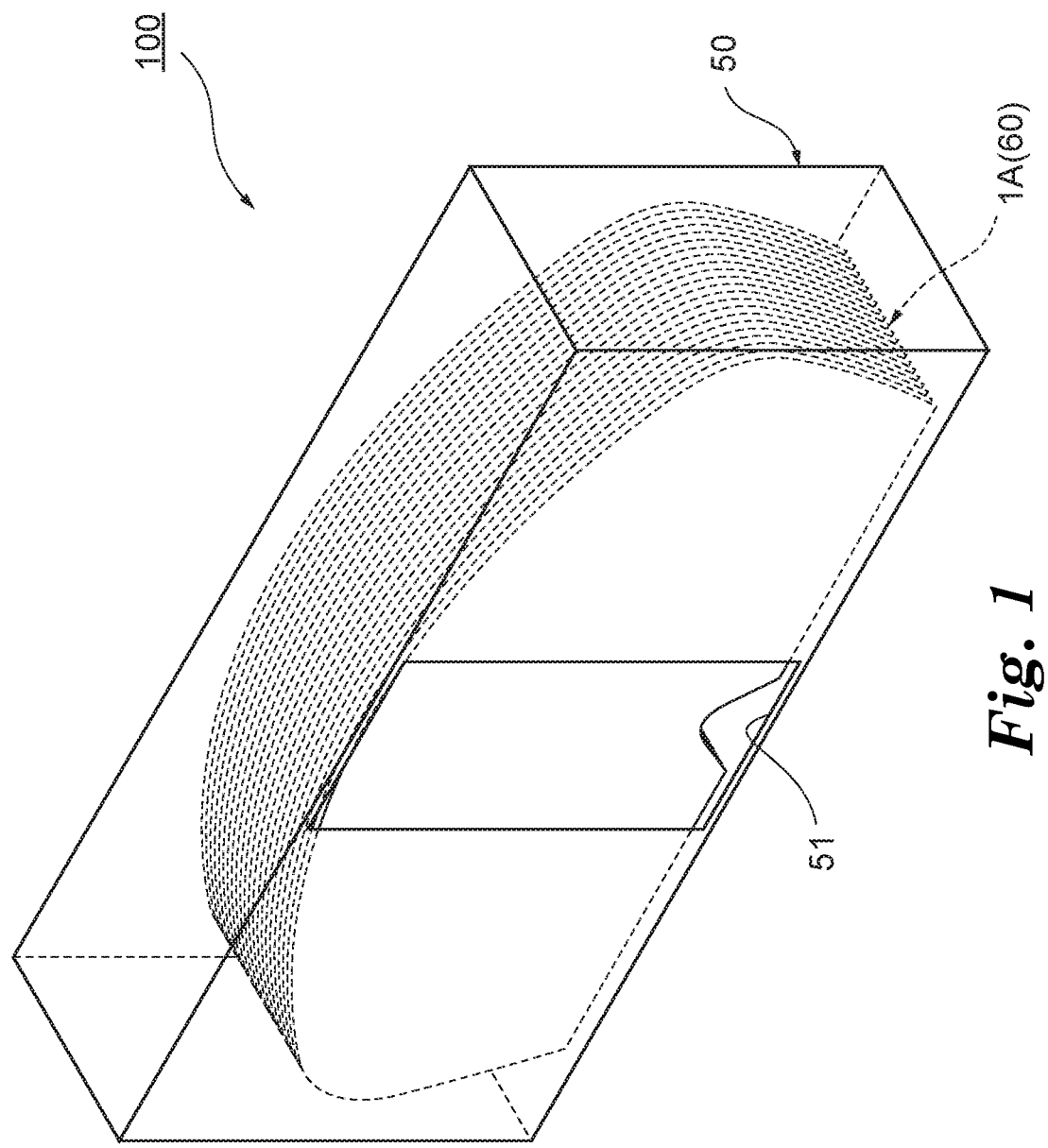
FIG. 1 is a perspective view illustrating a dispenser according to a first embodiment of the present invention.

Embodiments of the present invention are described below in detail while referring to the drawings. In the following description, the same or corresponding elements are given the same reference numeral, and duplicate explanations are omitted. Additionally, in the following description, the terms "upper" and "lower" are used, based on a state where a user is wearing a shield and a non-woven mask.

FIG. 1 is a perspective view illustrating a dispenser 100 according to a first embodiment of the present invention. As illustrated in FIG. 1, the dispenser 100 is provided with a shield 1A for use with a non-woven mask 2, and a container 50 configured to house a plurality of the shields 1A. The dispenser 100 stores the shields 1A housed in the container 50 and is capable of dispensing the shields 1A from the container 50 one at a time.

Figure 2:
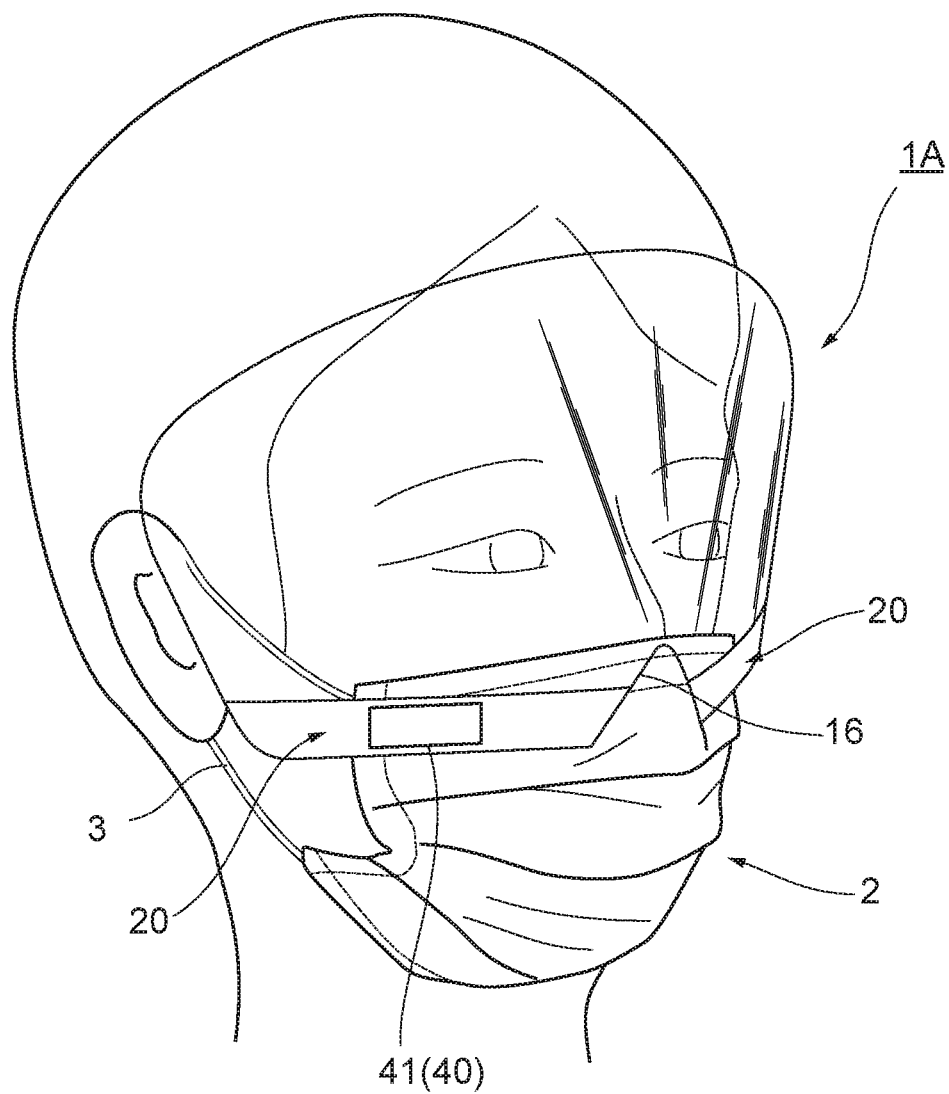
FIG. 2 is a perspective view illustrating an appearance of a shield when in use.
Figure 3A:
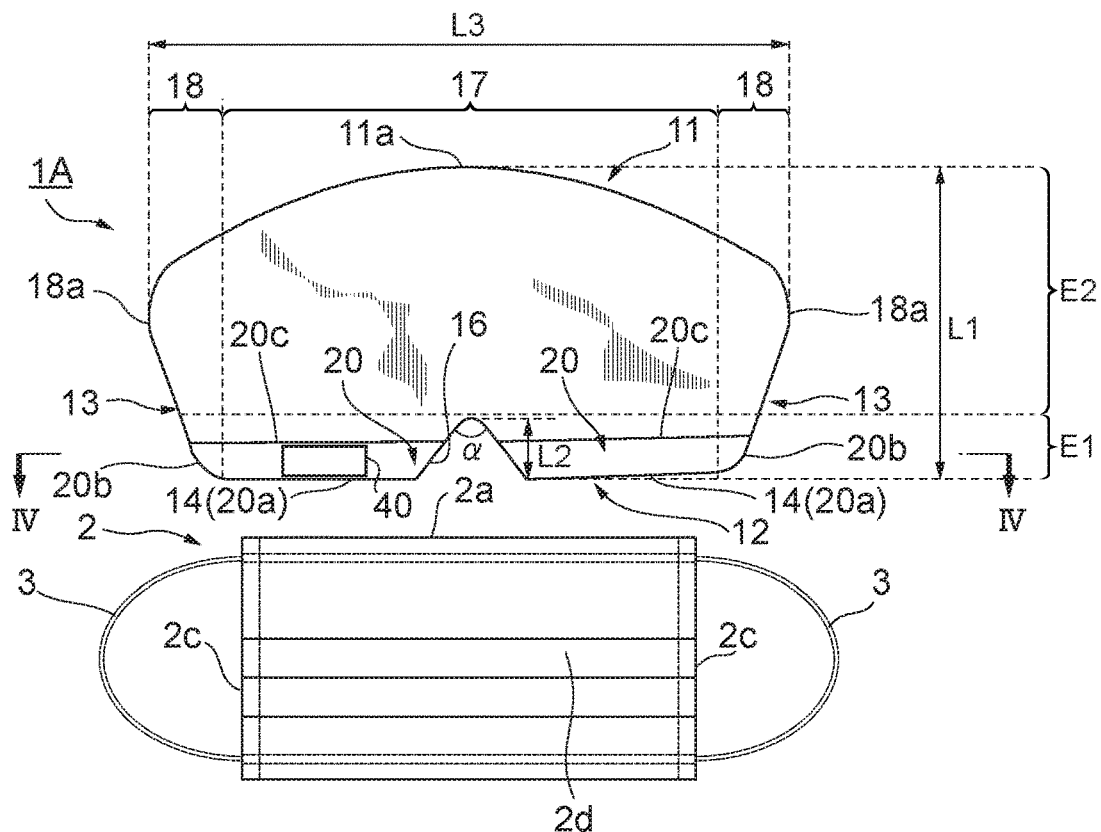
FIG. 3A is a front view illustrating a state prior to the shield being attached to a non-woven mask.
Figure 3B:
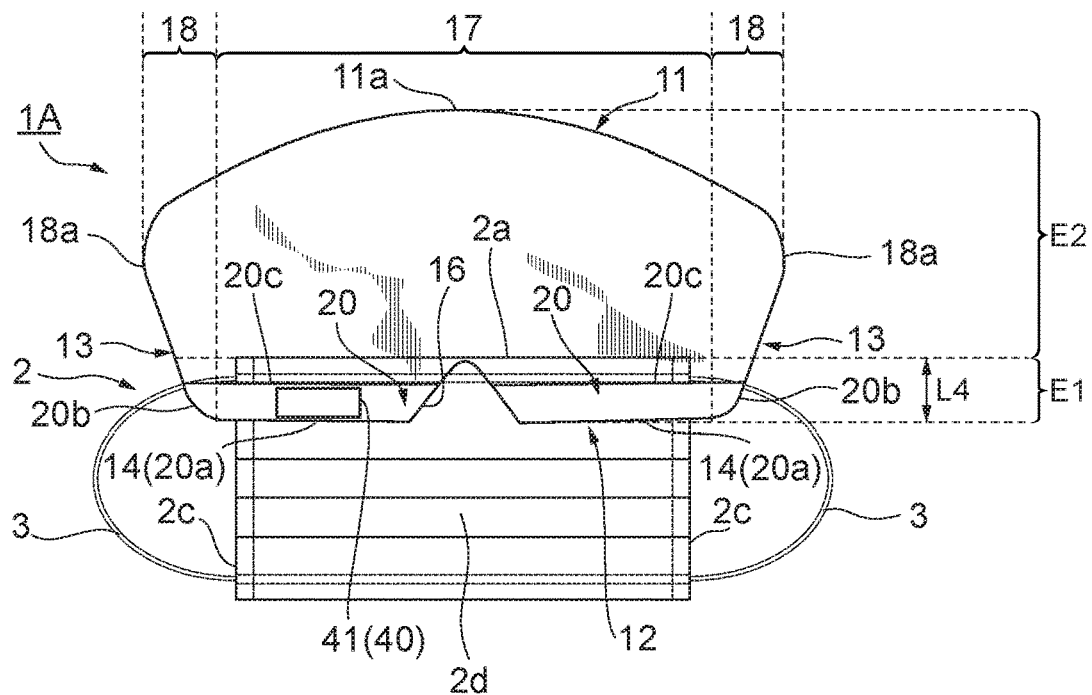
FIG. 3B is a front view illustrating a state where the shield is attached to a non-woven mask.

FIG. 2 is a perspective view illustrating an appearance of the shield 1A when in use. FIG. 3A is a front view illustrating a state prior to the shield being attached to the non-woven mask 2. FIG. 3B is a front view illustrating a state where the shield is attached to the non-woven mask 2. As illustrated in FIGS. 2, 3A, and 3B, the shield 1A is a member for protecting the area around the eyes of a user and is detachably attached to the non-woven mask 2, which covers the area around the mouth and nose of the user.

The non-woven mask 2 is formed from a rectangular mask member and may be constituted by a single member or by a multi-layer member. Additionally, the non-woven mask 2 may be provided with a flexible metal insert (not illustrated) along an edge portion 2a that is hung on the bridge of the nose. Rubber strings 3 for hanging on the ears are attached to both edge portions 2c, 2c in a width direction (a long side direction) of the non-woven mask 2. Note that the mode of attaching the non-woven mask 2 is not particularly limited and need not be an ear-hanging type, and may be a type that is attached by tying strings at the back the head. A front surface 2d of the non-woven mask 2 is a surface to which the shield 1A attaches. At least the front surface 2d of the non-woven mask 2 is constituted by non-woven fabric. However, a portion of the mask member constituting the non-woven mask 2 may include materials other than non-woven fabric.

The shield 1A is a member for protecting the eyes of a user wearing the non-woven mask 2. The shield 1A is provided with an attachment section E1 that is formed on the lower edge section 12 side of the shield 1A, overlaps with the non-woven mask 2, and attaches to the non-woven mask 2; and an eye protection section E2 that is formed on an upper edge section 11 side of the shield 1A and is capable of protecting the eyes of a user. The attachment section E1 on the lower edge section 12 side of the shield 1A overlaps with the front surface 2d of the non-woven mask 2 and detachably attaches to the non-woven mask 2 while the non-woven mask 2 is worn on a human body. In the attachment section E1, a connecting portion 20 detachably securing to the non-woven mask 2 is formed on a surface side, namely, a back surface E1a side (see FIG. 4), where the shield 1A overlaps with the non-woven mask 2. The shield 1 is formed from a flat member that is transparent and flexible. Polyester, acrylic acid resin, polycarbonate, polystyrene, and the like may be used as the material of the shield 1. A thickness of the polymer film from which the shield 1 is formed is from 0.05 to 0.25 mm and, most preferably, is 0.1 mm. The thickness imparts the desired flexibility to the shield 1. Herein, the term "flexibility" means that a modulus of elasticity of the material from which the shield 1 is formed is from about 400 to 7,000 MPa, preferably from about 1,200 to 5,000 MPa, and most preferably from about 1,350 to 3,500 MPa.

Next, a shape of the shield 1A according to the present embodiment is described. However, the shape and size of the shield 1A according to the embodiment are only examples and any configuration is possible provided that it is possible to attach the shield 1A to the non-woven mask 2 and protect the eyes of the user. As illustrated in FIGS. 3A and 3B, the shield 1A includes an edge, namely the lower edge section 12, of a side that connects to the non-woven mask 2 (that is, a lower side in a state where the non-woven mask 2 is being used); an edge on a side opposite the lower edge section 12, namely the upper edge section 11 (that is, a tip end section on an upper side in a state where the non-woven mask 2 is being used); and edges in the width direction of the non-woven mask 2, namely both edge sections 13, 13.

The upper edge section 11 widens in the width direction of the shield 1A so as to form an arch that bulges toward the side opposite the lower edge section 12, at a position separated from the edge section 2a of the non-woven mask 2 when attached. A dimension L1 between an apex 11a of the upper edge section 11 (the point separated farthest from the edge section 2a of the non-woven mask 2) and the lower edge section 12 is not particularly limited, but is set to 100 to 150 mm. An extending section 14 extending in the width direction is formed in the lower edge section 12 of the shield 1A, and a V-shaped cutout 16 is formed at a central position in the width direction. That is, the cutout 16 is formed in the lower edge section 12 of the shield 1A, at a position in the non-woven mask 2 corresponding to the portion covering the nose. A depth dimension L2 of the cutout 16 is not particularly limited, but is set to 10 to 25 mm. Additionally, an angle α of the cutout 16 is not particularly limited, but is set to 45 to 135°. The extending section 14 is formed on both sides in the width direction, thereby sandwiching the cutout 16 at the central position. In the present embodiment, the extending sections 14 extend farther outward than the both edge portions 2c, 2c of the non-woven mask 2 when attached. Additionally, the both edge sections 13, 13 extend at an inclination so as to widen toward the upper edge section 11 side. The shield 1A is divided into a base section 17, which is a region near the central position in the width direction and is provided at a position corresponding to the eyes of the user; and lateral sections 18, which are provided on both sides in the width direction of the base section 17. The lateral sections 18 are configured to extend toward the ear side of the user at a time of use. A dimension L3 between tip portions 18a, 18a in the width direction of the lateral sections 18, that is, a total length in the width direction of the shield 1A, is not particularly limited, but is set to 180 to 350 mm. In the shield 1A described above, at least a region more to the lower edge section 12 side than the central position in the vertical direction is defined as the attachment section E1. Additionally, a region more to the upper edge section 11 side than the attachment section E1 is defined as an eye protection section E2.

FIG. 4 is a drawing schematically illustrating a cross-section taken along a line IV-IV of the shield 1A depicted in FIG. 3A. Note that FIG. 4 is a drawing for explaining the cross-sectional structure in the width direction of the shield 1A of the attachment section E1, and the dimensional ratios of the shield 1A in FIG. 4 do not necessarily match those described herein. As illustrated in FIG. 4, a connecting portion 20 is formed on a back surface E1a side of the attachment section E1, and joining means 40 are provided on a front surface E1b side of the attachment section E1.

Next, the connecting portion 20 of the shield 1A is described. As illustrated in FIGS. 3A, 3B, and 4, the connecting portion 20 connects to the non-woven mask 2 and, thereby, attaches the shield 1A to the non-woven mask 2. The connecting portion 20 is capable of releasing the connection with the non-woven mask 2 and, via this releasing, the shield 1A can be removed from the non-woven mask 2. Additionally, the connecting portion 20 may be configured to be capable of repeated performance of the connecting and releasing with respect to the non-woven mask 2. In this case, the shield 1A can be repeatedly attached to and detached from the non-woven mask 2. Additionally, the shield 1A is secured to the non-woven mask 2 by the connecting portion 20 at a degree of strength (connecting strength) whereby the shield 1A can be detachably attached to the non-woven mask 2 while the non-woven mask 2 is worn on a human body. Due to this connecting strength, a configuration is achieved in which the shield 1A can be attached to the non-woven mask 2 via the connecting portion 20 while the non-woven mask 2 is being worn by the user, and the shield 1A can be detached from the non-woven mask 2 while the non-woven mask 2 is being worn by the user. The connecting strength of the connecting portion 20 is set to a degree of strength whereby the shield 1A will not fall off when the connecting portion 20 of the shield 1A is connected to the non-woven mask 2 while the non-woven mask 2 is being worn by the user. Note that the connecting strength is preferably set to a degree of strength whereby the shield 1A will not fall off, even in cases where the user performs work and moves their head while the shield 1A is attached to the non-woven mask 2. Additionally, the connecting strength is set to a degree of strength whereby the shield 1A can be removed by pulling on the shield 1A without applying excessive force, while the non-woven mask 2 is worn by the user. Additionally, the connecting strength may be set to a degree of strength whereby the shield 1A can be removed without excessively damaging (e.g. tearing, ripping, excessive fluffing of the surface, and the like of the non-woven mask 2) the non-woven mask 2 when removing the shield 1A.

The connecting portion 20 is formed on the attachment section E1 of the shield 1A. Additionally, the connecting portion 20 is formed on the surface side where the shield 1A overlaps with the non-woven mask 2, namely the back surface E1a (the surface facing the eyes of the user when worn) side. The connecting portion 20 is constituted by fixing a flat member capable of connecting to the non-woven mask 2 on the back surface E1a side of the attachment section E1 of the shield 1A. In the present embodiment, the connecting portion 20 is formed so as to extend along the extending section 14 of the lower edge section 12. The connecting portion 20 is formed in substantially all regions in the width direction of the shield 1A. The connecting portion 20 is formed so as to extend in a band shape with a predetermined width. The width of the connecting portion 20 may be set to about 90 to 110 mm, and a total length of the connecting portion 20 may be set to about 180 to 220 mm (in the present embodiment, the connecting portion 20 is split into two by the cutout 16 and, thus, the total length of the two). In the present embodiment, an edge portion 20a of the lower side of the connecting portion 20 matches the extending section 14 of the lower edge section 12 of the shield 1A, and edge portions 20b, 20b of the connecting portion 20 match the edge portions 13, 13 of the shield 1A. With such a configuration, the connecting portion 20 is formed at positions corresponding to substantially all regions in the width direction of the non-woven mask 2, including positions corresponding to the both edge portions in the width direction of the non-woven mask 2.

When attaching the shield 1A to the non-woven mask 2, the attachment section E1 of the shield 1A is overlapped with the front surface 2d of the non-woven mask 2, and the connecting portion 20 is pressed so as to be connected to the front surface 2d of the non-woven mask 2. Note that the size of the attachment section E1 (the amount of overlap of the shield 1A with the non-woven mask 2), that is, where (how far from the edge portion 2a of the non-woven mask 2) the connecting portion 20 is connected to the front surface 2d of the non-woven mask 2 is not particularly limited and any range is possible, provided that the eyes of the user can be sufficiently covered by the shield 1A. For example, a dimension L4 of the region, namely the attachment section E1, where the shield 1A overlaps with the non-woven mask 2, may be set to about 15 to 50 mm (see FIG. 3B). However, a boundary line between the attachment section E1 and the eye protection section E2 need not be clearly stipulated on the product. It is sufficient that at least the region more to the lower edge section 12 side than the upper edge section 20c of the connecting portion 20 functions as the attachment section E1. Note that a visible mark indicating the attachment section E1 (that is, a visible mark indicating the amount of overlap of the shield 1A on the non-woven mask 2) may be shown on the shield 1A. Additionally, depending on the attachment method of the user, a portion of the eye protection section E2 may overlap with the non-woven mask 2. The shield 1A is preferably disposed so that a center line in the width direction of the shield 1A and a center line in the width direction of the non-woven mask 2 substantially match. Additionally, the cutout 16 is preferably disposed at a position corresponding to the portion of the non-woven mask that covers the nose.

Figure 5:
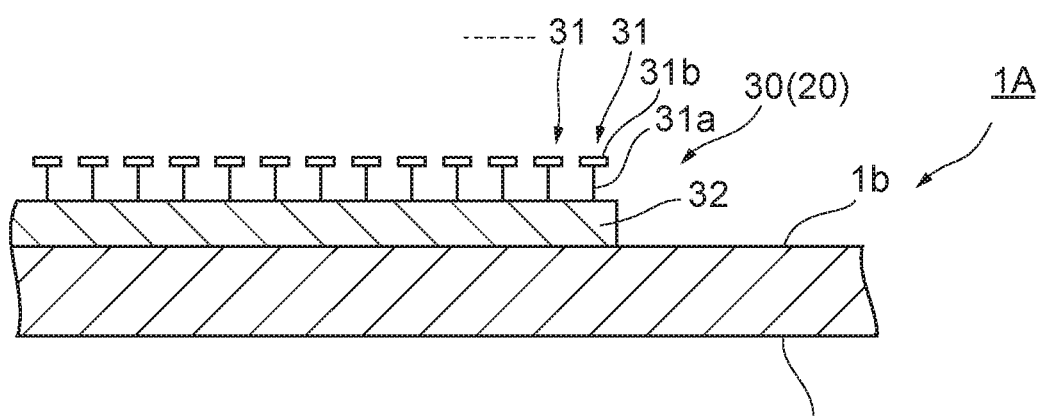
FIG. 5 is a schematic cross-sectional view of a case where mechanical engagement means are used as a connecting portion.

Any configuration can be used for the configuration of the connecting portion 20, provided that connection with the front surface 2d of the non-woven mask 2 is possible. Specifically, the connecting strength of the connecting portion 20 to the non-woven mask 2 is preferably 0.05 N or greater. As illustrated in FIG. 5, the connecting portion 20 is constituted by mechanical engagement means 30. Examples of the mechanical engagement means 30 include surface fasteners (mechanical fasteners) and the like. The mechanical engagement means 30 have a construction in which a plurality of male engagement elements (hooks) 31 is formed integrally with a base member 32, and each of the male engagement elements 31 is provided directly on the base member 32. A back surface of the base member 32 of the mechanical engagement means 30 (a surface opposite the surface where the male engagement elements 31 are formed) is fixed to the back surface of the shield 1A by an adhesive agent, an adhesive material, or the like. The fixing strength of this portion is at least greater than the connecting strength of the connecting portion 20 to the non-woven mask 2. Note that from the perspectives of not excessively increasing the connecting strength, suppressing damage to the non-woven mask 2 when removing the shield 1A, and detachable fixing the shield 1A to the non-woven mask 2, the mechanical engagement means 30 preferably have a connecting strength to the non-woven mask 2 of 0.05 N or greater. On the other hand, an upper limit of the connecting strength is not particularly limited and, generally, any mechanical engagement means 30 that a person skilled in the art would normally use with non-woven fabric can be used. Note that in an aspect, the upper limit of the connecting strength may be set to 1.5 N or less.

In the present specification, the connecting strength is a value measured as follows. First, the non-woven mask 2 and the shield 1A are overlapped so that the width direction of the non-woven mask 2 and the width direction of the shield 1A are parallel. At this time, at least a portion of the connecting portion 20 overlaps the non-woven mask 2. Then, a cylindrical roller that has a smooth surface and a mass of 1 kg is passed back and forth twice, thus connecting the non-woven mask 2 and the shield 1A. Next, while the non-woven mask 2 is secured in a jig, the shield 1A is grabbed by the clip of a tensile tester, and the shield 1A is peeled up from the non-woven mask 2 in a 90-degree direction and at a speed of 300 mm/min. The force needed at this time is defined as the "connecting strength of the connecting portion 20 to the non-woven mask".

Figure 7A:
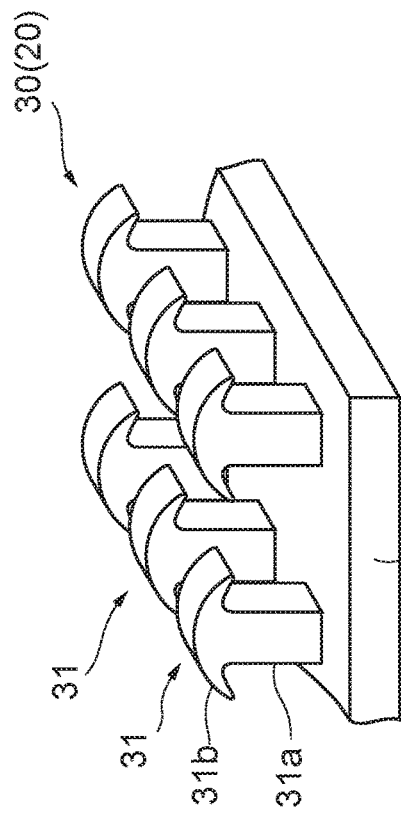
FIGS. 7A to 7D are drawings illustrating examples of the mechanical engagement means.
Figure 7B:
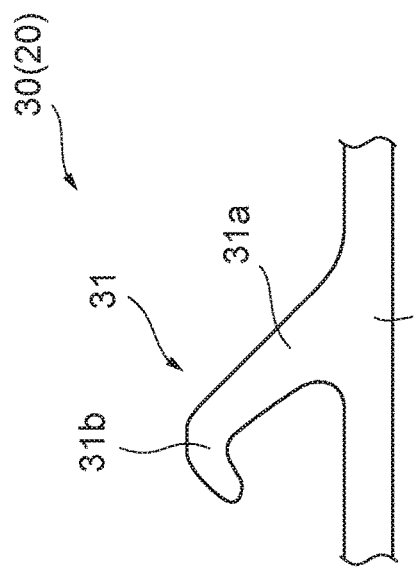
Figure 7C:
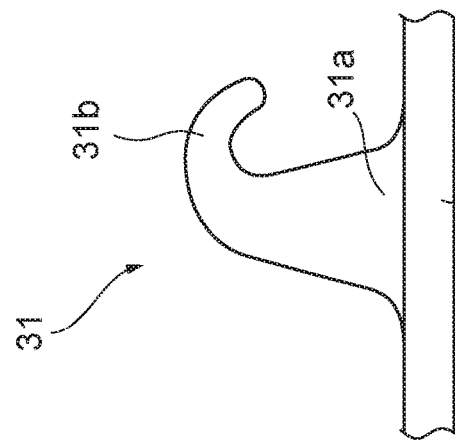
Figure 7D:
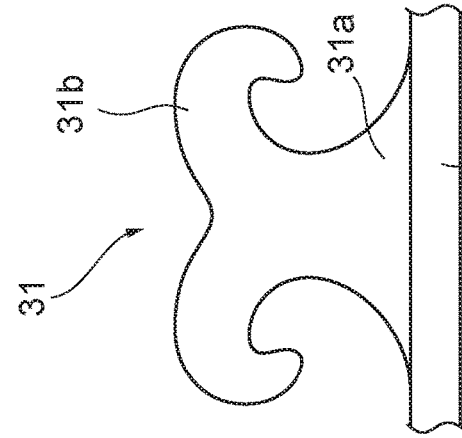

As illustrated in FIG. 5, the male engagement elements 31 according to the present embodiment are provided with a column portion 31a that extends from the base member 32 and a head portion 31b formed at the tip of the column portion 31a. However, the shape of the male engagement elements 31 is not particularly limited, and may be set as appropriate according to the dimensions (length, width) or degree of extensibility of the mechanical engagement means 30. For example, as illustrated in FIG. 6A, the male engagement elements 31 may be provided with a cylindrical column portion 31a and a semi-spherical head portion 31b. Note that the head portion 31b may be a portion provided with a plurality of grooves in a circular plate as illustrated in FIG. 6B, or may have a circular plate shape as illustrated in FIG. 6C. Alternatively, as illustrated in FIG. 7A, the male engagement elements 31 may be provided with a prism shape column portion 31a and an arrowhead shape head portion 31b. Additionally, as illustrated in FIG. 7B, the male engagement elements 31 may be provided with a column portion 31a extending diagonally upward and a head portion 31b that bends diagonally downward from the tip of the column portion 31a. Additionally, as illustrated in FIG. 7C, the male engagement elements 31 may be provided with a column portion 31a extending upward and a head portion 31b extending so as to curve in one direction of the lateral direction from the top edge of the column portion 31a, wherein an entirety of the male engagement element 31 forms a J-shape. Additionally, as illustrated in FIG. 7D, the male engagement elements 31 may be provided with a column portion 31a extending upward and a head portion 31b that is bifurcated and extends so as to curve in both directions of the lateral direction from the top edge of the column portion 31a.

A height of the male engagement elements 31 may be from 0.25 to 0.75 mm, or may be from 0.38 to 0.68 mm. Additionally, a density of the male engagement elements 31 may be from 140 to 372 elements/cm$^2$ (from 900 to 2400 elements/in$^2$), or may be from 140 to 248 elements/cm$^2$ (from 900 to 1600 elements/in$^2$). Note that the height of the male engagement elements 31 indicates a distance from a surface of the base member 32 to an apex (tallest position) of the head portion 31b of the male engagement elements 31, and is a dimension indicated as "H" in, for example, FIG. 6A. When the height is within this range, regardless of the shape of the male engagement elements 31, a suitable connecting strength needed for the connecting portion 20 of the shield 1A can be ensured. Additionally, when a user attaches the shield 1A while wearing the non-woven mask 2, the shield 1A can be connected to the non-woven mask 2 with a light pressing, without excessively pressing the connecting portion 20 against the non-woven mask 2. Additionally, the shield 1A will not peel off even if the user shakes their head while the shield 1A is attached to the non-woven mask 2. Moreover, when removing the shield 1A, the user can remove the shield 1A with force equivalent to that of pulling with one hand. Additionally, the shield 1A can be removed in a manner that does not leave noticeable damage on the non-woven mask 2 when the shield 1A is removed. In cases where the connecting strength is less than that obtained at the numerical ranges described above, it is difficult to maintain an attached state of the shield 1A to the non-woven mask 2. In cases where the connecting strength is greater than that obtained at the numerical ranges described above, there is a possibility that damage will be left in the non-woven mask 2 when the shield 1A is removed.

The extendable mechanical engagement means 30 is made of a thermoplastic resin or the like, examples of which include a mixture of polypropylene (PP) resin and polyethylene (PE) resin, and ethylene-vinyl acetate (EVA) copolymer. If a mixture of PP and PE is used, the weight ratio of PP to PE may be roughly 95:5 to 30:70. If the amount of PP exceeds this maximum, the properties of the PP will predominate, tending to cause the engagement elements to become stiff. Conversely, if the amount of PP falls below the minimum, the engaging power of the male engagement elements 31 will be weakened. The PP may be a homopolymer or a copolymer. Examples of PE include low density polyethylene (LDPE), high density polyethylene (HDPE), and linear low density polyethylene (LLDPE).

Next, the joining means 40 of the shield 1A is described. As illustrated in FIG. 4, the joining means 40 is detachably joined to mechanical engagement means formed on another shield 1A. In the present embodiment, the joining means 40 includes a joining member 41 that is detachably joined to the male engagement elements 31. Specifically, the joining member 41 is constituted of non-woven fabric. Note that, provided that the joining member 41 can be joined in a mechanically removable manner to the male engagement elements 31, the joining member 41 is not particularly limited to the non-woven fabric, and examples thereof may include surface fasteners including female engagement elements and surface fasteners including male engagement elements. In this case, handling is easy because these members will not be joined to other members (that is, not be joined to members without the female engagement elements) even if they unintentionally come in contact with other members when being used.

The joining member 41 is provided in a region on a first side in the width direction of the shield 1A, on the front surface E1b side of the attachment section E1 of the shield 1A. In the figures, the joining member 41 is provided in the left-side region when viewing from the front surface side of the shield 1A, but there are also shields 1A in which the joining member 41 is provided in the right-side region when viewing from the front surface side of the shield 1A. The joining member 41 is provided in a region on a first side in the width direction of the shield 1A, near a central section of a roughly trisected area from the edge portion 13 of the shield to the cutout 16 (see FIGS. 3A and 3B). Additionally, the joining member 41 is provided in substantially all regions in the vertical direction of the attachment section E1. Note that the position and size of the joining member 41 may be appropriately adjusted depending on the engagement strength to the male engagement elements 31. For example, the joining portion 41 may be provided in substantially all regions from the edge portion 13 of the shield to the cutout 16, or may be provided in a portion of the regions in the vertical direction of the attachment section E1.

Figure 8:
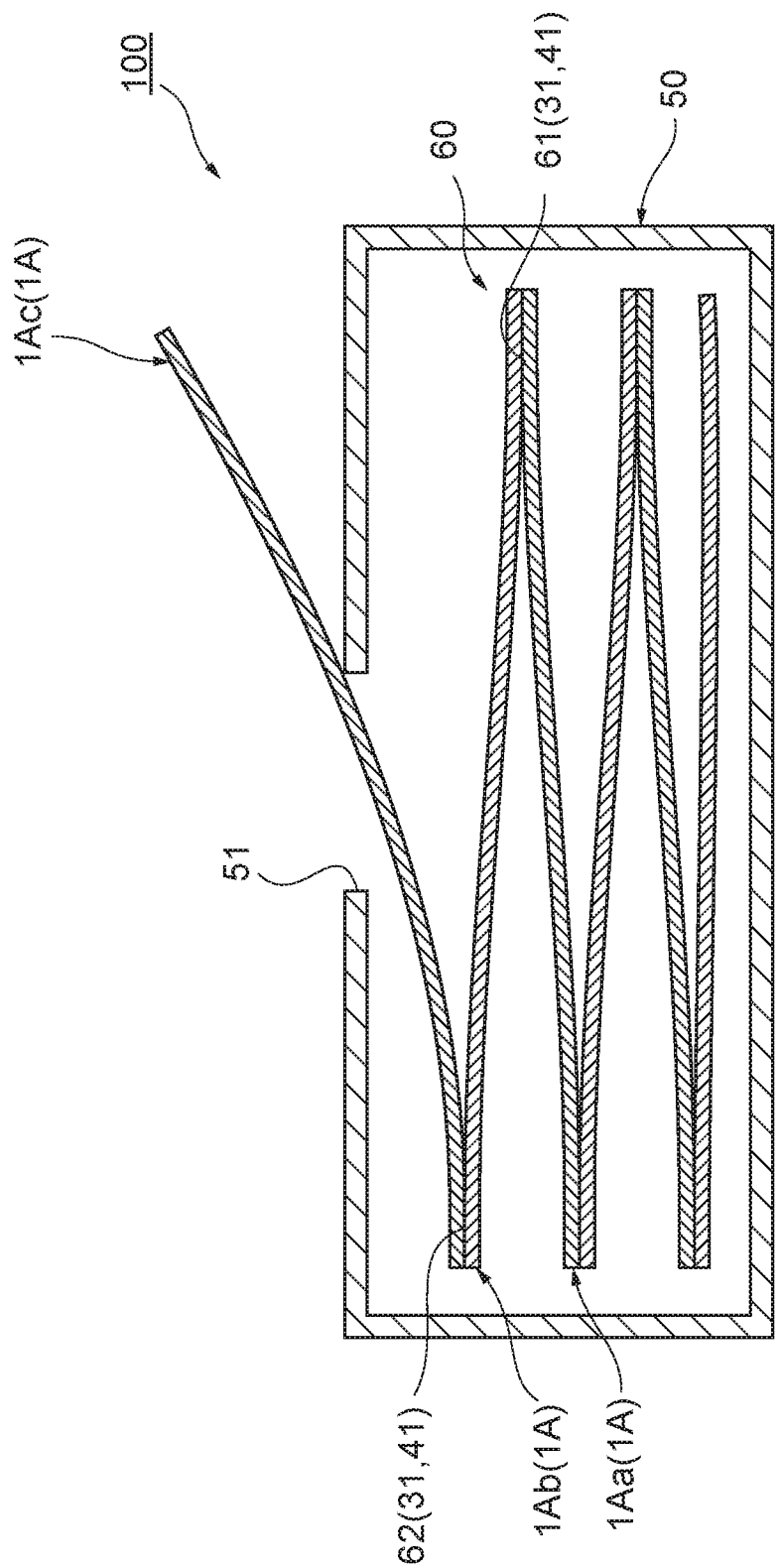
FIG. 8 is a drawing for explaining operations at a time of use of the dispenser.

As illustrated in FIGS. 1, 4, and 8, due to the fact that the connecting portion 20 and the joining means 40 are joined, a plurality of the shields 1A are stacked in a mutually detachable joined state, and a stacked body 60 is formed. That is, the connecting portion 20 functions both as the connection with the non-woven mask 2 and also as the joint with the other shield 1A. The plurality of shields 1A are stacked in the stacked body 60 such that shields 1A, for which the regions where the joining members 41 are formed differ from each other, are adjacent. Specifically, with the stacked body 60, a shield 1A in which the joining member 41 is provided in the right-side region when viewing from the front surface side of the shield 1A is stacked on a shield 1A in which the joining member 41 is provided in the left-side region when viewing from the front surface side of the shield 1A, and a shield 1A in which the joining member 41 is provided in the left-side region when viewing from the front surface side of the shield 1A is stacked thereon. This left-right alternating arrangement (zig-zag arrangement) is repeated in the same manner thereafter. The shields 1A are housed in the container 50 in the stacked body 60 state.

More specifically, for example, in the stacked body 60 including at least three of the shields 1A, these three shields 1A are referred to as a first shield 1Aa, a second shield 1Ab, and a third shield 1Ac. The first shield 1Aa and the third shield 1Ac are the shield 1A in which the joining member 41 is provided in the left-side region when viewing from the front surface side of the shield 1A. In contrast, the second shield 1Ab is the shield 1A in which the joining member 41 is provided in the right-side region when viewing from the front surface side of the shield 1A. The first shield 1Aa, the second shield 1Ab, and the third shield 1Ac are stacked in this order toward one direction of a stacking direction. Note that, in the present embodiment, the stacking direction is a direction in which one shield 1A is stacked on the front surface side of another shield 1A. Additionally, conversely, the stacking direction may be defined as a direction in which one shield 1A is stacked on the back surface side of another shield 1A. The first shield 1Aa, the second shield 1Ab, and the third shield 1Ac are stacked such that the front/back, the vertical direction positions, and the width direction positions thereof match. Here, the third shield 1Ac is defined as the uppermost shield 1A of the stacked body 60. In this case, the joining member 41 of the first shield 1Aa and the male engagement elements 31 of the connecting portion 20 of the second shield 1Ab are mutually detachably joined. As such, the first shield 1Aa and the second shield 1Ab are mutually detachably joined at a section (hereinafter, the "first joining section 61") positioned in a region on a first side in the width direction of the shield 1A. Additionally, the joining member 41 of the second shield 1Ab and the male engagement elements 31 of the connecting portion 20 of the third shield 1Ac are mutually detachably joined. As such, the second shield 1Ab and the third shield 1Ac are mutually detachably joined at a section (hereinafter, the "second joining section 62") positioned in a region on a second side opposite the first side in the width direction of the shield 1A. That is, the first joining section 61 and the second joining section 62 are constituted by the connecting portion 20 formed by the mechanical engagement means including the male engagement elements 31, and a joining member 41 that is provided on the front surface E1b side of the attachment section E1 and that detachably joins with the mechanical engagement means.

Note that the phrase "detachably join" means that sliding and the like of the shields 1A against each other in the container 50 is suppressed and the shields 1A are joined at a degree of strength whereby a user can easily dispense the shields 1A; specifically, that the shields 1A are joined at a strength of 0.05 N or greater. This strength is defined by the force required to pull one shield 1A until the next shield 1A protrudes out of the container 50. That is, in cases where the shields 1A are joined at a strength less than the strength described above, it will not be possible to pull the next shield 1A out. Additionally, preferably, the shields 1A may be joined at a strength of 2.0 N or less. In cases where the shields 1A are joined at a strength greater than the strength described above, the joining force will be too strong and the container 50 may be damaged, or removal by hand will be difficult and the shields may be damaged when forcibly removed.

Next, the container 50 is described. As illustrated in FIGS. 1 and 8, the container 50 exhibits a rectangular parallelepiped form with slightly larger dimensions in the vertical direction and the width direction than the dimensions in the vertical direction and the width direction of the shield 1A. Additionally, a dimension in a depth direction of the container 50 is a dimension that is slightly larger than a thickness of the stacked body 60 to be housed (that is, a thickness calculated on the basis of the product of the thickness of one of the shields 1A to be housed and the maximum number of shields (e.g. about 20 to 60 shields)). The container 50 houses the stacked body 60 in an erected state.

The container 50 includes a dispensing opening (dispensing means) 51 through which the shields 1A can pass. Specifically, the container 50 includes the dispensing opening 51 that is open between positions, each covering the first joining section 61 and the second joining section 62, in the stacking direction of the stacked body 60 in a state in which the stacked body 60 is stored. Here, the phrase "positions, each covering the first joining section 61 and the second joining section 62," refer to positions in the container 50 that overlap with each of the first joining section 61 and the second joining section 62 of the stacked body 60 when viewed in the stacking direction of the stacked body 60. Additionally, the term "between" when used in the context of "between positions" refers to a region in the width direction of the shield 1A (that is, the width direction of the stacked body 60) sandwiched by the positions. In the present embodiment, the container 50 includes the dispensing opening 51 that is open on a front surface thereof. Moreover, when viewed in the stacking direction of the container 50, the container 50 includes the dispensing opening 51 for which both edges in the width direction are defined by a wall portion formed including a region overlapping with the first joining section 61 of the housed stacked body 60, and a wall portion formed including a region overlapping the second joining section 62 of the housed stacked body 60. Here, the first joining section 61 and the second joining section 62 are each positioned in the region on the first side in the width direction of the shield 1A and the region on the second side opposite the first side in the width direction of the shield 1A. Therefore, the dispensing opening 51 is open at a region near the center in the width direction of the container 50. Note that the dispensing opening 51 is open in a vertical direction thereof so as to cross in a direction orthogonal to the width direction of the shield 1A, from near the top edge to near the bottom edge of the container 50. Note that the shape of the dispensing opening 51 is not limited to a rectangular shape, and the sides may be formed from arcs.

Next, the actions and effects of the dispenser 100 and the shield 1A according to the first embodiment are described.

With the dispenser 100 according to the first embodiment, the plurality of shields 1A are stored in a mutually detachable joined state in the container 50. As such, sliding and the like of the plurality of shields 1A against each other in the container 50 is suppressed and, therefore, sticking of the shields 1A to each other due to the generation of static electricity is suppressed. Thus, a user can easily dispense the shields 1A from the dispensing opening 51 of the container 50.

Additionally, with the dispenser 100 according to the first embodiment, a stacked body 60 includes at least a first shield 1Aa, a second shield 1Ab, and a third shield 1Ac stacked in this order in one direction of a stacking direction. The first shield 1Aa and the second shield 1Ab are mutually detachably joined at a first joining section 61 positioned in a region on a first side in a width direction of the shields 1A. The second shield 1Ab and the third shield 1Ac are mutually detachably joined at a second joining section 62 positioned in a region on a side opposite the first side in the width direction, namely a second side, of the shields 1A. The container 50 includes a dispensing opening 51 between positions, each covering the first joining section 61 and the second joining section 62, in the stacking direction in a state in which the stacked body 60 is stored.

Figure 9:
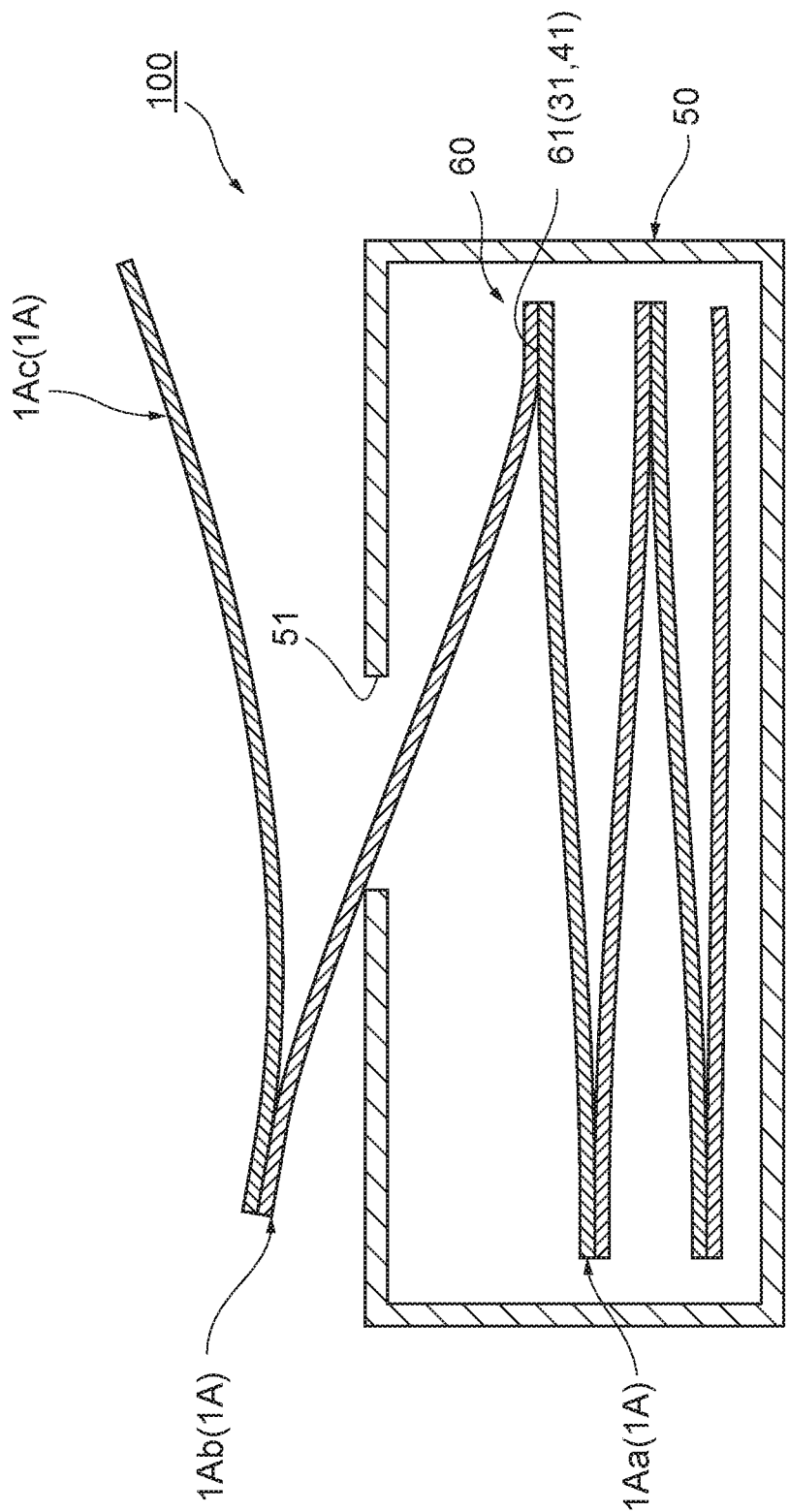
FIG. 9 is a drawing for explaining operations at a time of use of the dispenser.

FIGS. 8 and 9 are drawings for explaining operations at a time of use of the dispenser 100. The dispenser 100 is provided with the configuration described above. As such, as illustrated in FIG. 8, in a case where an uppermost shield 1A of the stacked body 60 is the third shield 1Ac, first, the region on the side opposite the second joining section 62 in the width direction of the third shield 1Ac is in a state protruding out from the dispensing opening 51 of the container 50. Then, when the user grabs and pulls the third shield 1Ac, the region on the second joining section 62 side in the width direction of the third shield 1Ac is pulled out and, at the same time, the second shield 1Ab follows via the second joining section 62 and is pulled out. As a result, the region on the second joining section 62 side in the width direction of the second shield 1Ab (that is, the region on the side opposite the first joining section 61) assumes a state protruding out from the dispensing opening 51 of the container 50.

Next, a specific aspect of the aforementioned operations is described. For example, in cases where the right-side region of the third shield 1Ac is in a state protruding out from the dispensing opening 51 of the container 50, the user pulls out the third shield 1Ac in, for example, the right direction. Here, the second shield 1Ab is connected to the third shield 1Ac at the left edge side, and is connected to the first shield 1Aa at the right edge side. As such, at this time, the second shield 1Ab flexes (elastically deforms) so as to become convex toward the dispensing opening 51, and this flexed state continues until the second joining section 62 protrudes out of the container 50. Then, when the second joining section 62 of the second shield 1Ab protrudes out of the container 50, the state of the second joining section 62 being restrained by the left side of the dispensing opening 51 is released and, as a result, forces act to return the flexing to its original state (see FIG. 9). Note that following these operations, the user pulls the third shield 1Ac in, for example, a direction orthogonal to the dispensing direction or in the left direction to release the joining of the second joining section 62.

Then, likewise, when the user grabs and pulls the second shield 1Ab, the region on the first joining section 61 side in the width direction of the second shield 1Ab is pulled out and, at the same time, the first shield 1Aa follows via the first joining section 61 and is pulled out. As a result, the region on the first joining section 61 side in the width direction of the first shield 1Aa assumes a state protruding out from the dispensing opening 51 of the container 50. The specific aspect of the operations described above is the same for a case in which the third shield 1Ac described above is pulled out. According to this dispenser 100, by continuing and repeating the same operations, the shields 1A can be easily dispensed without touching the other shields 1A. Thus, continuous dispensing of the shields 1A is possible due to the joining sections being arranged at mutually different positions across the dispensing opening 51.

Additionally, with the dispenser 100 according to the first embodiment, the shield 1A includes an attachment section E1 that is formed on a lower edge section 12 side of the shield 1A, overlaps with the non-woven mask 2, and attaches to the non-woven mask 2. In the attachment section E1, a connecting portion 20 detachably securing to the non-woven mask 2 is formed in substantially all regions in the width direction of the shield 1A, on a surface side, namely a back surface E1a side, where the shield 1A overlaps with the non-woven mask 2. As such, because the connecting portion 20 is formed on the lower edge section 12 side of the shield 1A, an excellent field of view of the user can be ensured while using the shield 1A. Additionally, because the connecting portion 20 is formed in substantially all regions in the width direction of the shield 1A, it is possible to reliably detachably secure the shield 1A to the non-woven mask 2.

Additionally, with the dispenser 100 according to the first embodiment, the first joining section 61 and the second joining section 62 are constituted by the connecting portion 20 that is formed by mechanical engagement means including male engagement elements 31, and joining member 41 that is provided on a front surface E1b side of the attachment section E1 and that detachably joins with the mechanical engagement means. In this case, because the connecting portion 20 is formed by the mechanical engagement means including the male engagement elements 31, connecting strength will not easily decline, even when the shield 1A is repeatedly attached to and detached from the non-woven mask 2. Additionally, because the mechanical engagement means do not function only as the connecting portion 20, but also function as a portion of the first joining section 61 and the second joining section 62, the configuration of the shield 1A can be simplified.

Additionally with the shield 1A according to the first embodiment, because the connecting portion 20 is formed on the lower edge section 12 side of the shield 1A, an excellent field of view of the user can be ensured while using the shield 1A. Additionally, because the connecting portion 20 is formed in substantially all regions in the width direction of the shield 1A, it is possible to reliably detachably secure the shield 1A to the non-woven mask 2. Additionally, because the connecting portion 20 is constituted from the mechanical engagement means including the male engagement elements 31, connecting strength will not easily decline, even when the shield 1A is repeatedly attached to and detached from the non-woven mask 2.

Figure 10:
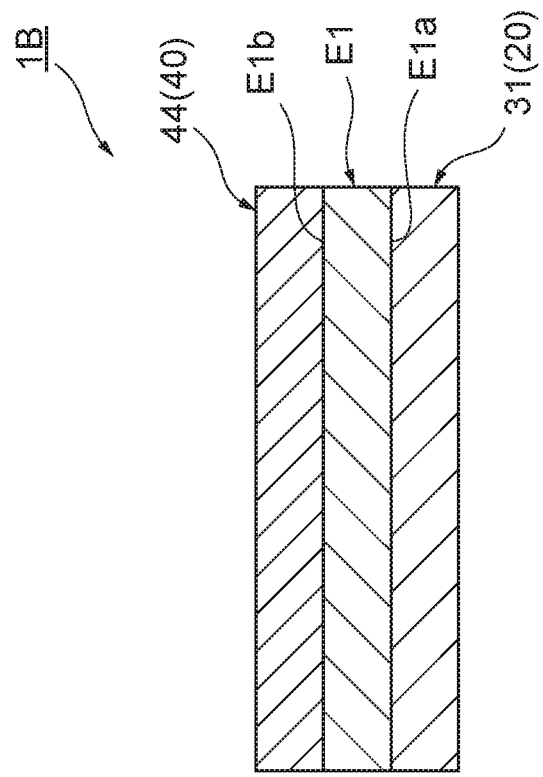
FIG. 10 is a drawing schematically illustrating a cross-section of a shield according to a second embodiment.

FIG. 10 is a drawing schematically illustrating a cross-section of a shield 1B used in a dispenser 100 according to a second embodiment. As illustrated in FIG. 10, the shield 1B used in the dispenser 100 according to the second embodiment differs from the shield 1A used in the dispenser 100 according to the first embodiment in that a second adhesive 44 is used instead of the non-woven fabric as the joining means 40 in the first joining section 61 and the second joining section 62. That is, in the shield 1B, the first joining section 61 and the second joining section 62 are constituted by the connecting portion 20 formed by the mechanical engagement means including the male engagement elements 31, and the second adhesive 44 that is provided on the front surface E1b side of the attachment section E1 and that detachably joins with the mechanical engagement means.

Examples of the second adhesive 44 include acrylic-based adhesives, synthetic rubber-based adhesives, and silicone adhesives. The second adhesive 44 is set such that a strength with respect to the connecting portion 20 is attained whereby the actions and effects of the dispenser 100 described previously can be advantageously provided. Specifically, in a case where the user pulls out the uppermost shield of the stacked body 60 from the container 50, the adhesive strength is set such that the next shield, which is joined to the uppermost shield, follows and is pulled out, and the joining therebetween is released due to frictional forces between the container 50 and the shields.

In this case, instead of the joining member 41 or similar non-woven fabric, the second adhesive 44 is used as the joining means 40. Here, because the thickness of the adhesive can be reduced, the first joining section 61 and the second joining section 62 can be formed thinly.

FIG. 11 is a drawing schematically illustrating a cross-section of a shield 1C used in a dispenser 100 according to a third embodiment. As illustrated in FIG. 11, the shield 1C used in the dispenser 100 according to the third embodiment differs from the shield 1A used in the dispenser 100 according to the first embodiment in that the connecting portion 20 is formed by a first adhesive 43 instead of the mechanical engagement means including the male engagement elements 31, and the second adhesive 44 is provided instead of the joining means 40 on the front surface E1b side of the attachment section E1. That is, in the shield 1C, the first joining section 61 and the second joining section 62 are constituted by the connecting portion 20 that includes the first adhesive 43, and the second adhesive 44 that is provided on the front surface E1b side of the attachment section E1.

Examples of the first adhesive 43 include acrylic-based adhesives, synthetic rubber-based adhesives, and silicone-based adhesives. The first adhesive 43 is appropriately set such that an appropriate degree of adhesive strength with respect to the non-woven mask 2 is attained.

In this case, adhesive strength between a region on the front surface E1b side of the attachment section E1 where the second adhesive 44 is provided and the connecting portion 20 that includes the first adhesive 43 is stronger than adhesive strength between a region on the front surface E1b side of the attachment section E1 where the second adhesive 44 is not provided and the connecting portion 20 that includes the first adhesive 43. Due to this difference in adhesive strengths, the region on the front surface E1b side of the attachment section E1 where the second adhesive 44 is provided and the connecting portion 20 that includes the first adhesive 43 function as the first joining section 61 and the second joining section 62. Here, because the thickness of the adhesives can be reduced, increases in the thicknesses of the first joining section 61 and the second joining section 62 can be suppressed.

Figure 12:
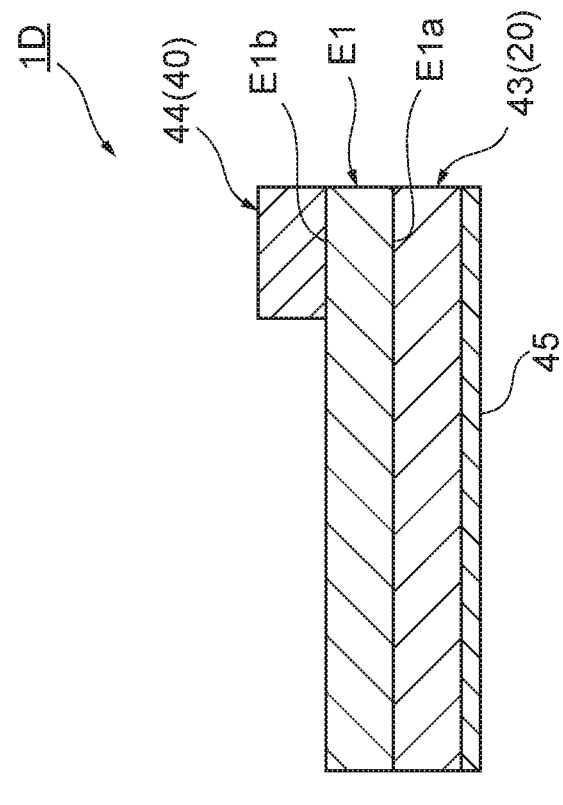
FIG. 12 is a drawing schematically illustrating a cross-section of a shield according to a fourth embodiment.

FIG. 12 is a drawing schematically illustrating a cross-section of a shield 1D used in a dispenser 100 according to a fourth embodiment. As illustrated in FIG. 12, the shield 1D used in the dispenser 100 according to the fourth embodiment differs from the shield 1C used in the dispenser 100 according to the third embodiment in that the shield 1D further includes a liner 45 that covers the entire surface of the first adhesive 43 on the surface side that overlaps with the non-woven mask 2. Additionally, the shield 1D illustrated in the drawings differs from the shield 1C in that the second adhesive 44 is only provided near the edge portion 20b of the connecting portion 20. Note that the region where the second adhesive 44 is provided is not limited to the position depicted in FIG. 12 and, for example, may be provided at the same position as the region where the second adhesive 44 is provided in the shield 1C (see FIG. 11).

A common release film may be used as the liner 45. Examples thereof include silicone-based release films, fluorosilicone-based release films, and the like. When the stacked body 60 is constituted by the shields 1D, the liner 45 is in an adhered state, covering the first adhesive 43. Additionally, the liner 45 is peeled from the first adhesive 43 when attaching the shield 1D to the non-woven mask 2.

In this case, the first joining section 61 and the second joining section 62 are constituted by the second adhesive 44. Here, because the thickness of the adhesive can be reduced, increases in the thicknesses of the first joining section 61 and the second joining section 62 can be suppressed.

FIG. 13 is a drawing schematically illustrating a cross-section of a shield 1E used in a dispenser 100 according to a fifth embodiment. As illustrated in FIG. 13, the shield 1E used in the dispenser 100 according to the fifth embodiment differs from the shield 1A used in the dispenser 100 according to the first embodiment in that the shield 1E does not include the joining means 40 on the front surface E1b side of the attachment section E1; the connecting portion 20 includes the first adhesive 43 and also a portion of the connecting portion 20 on the surface side that overlaps with the non-woven mask 2 is covered by the liner 45; and the remainder is exposed as the exposed portion 46. That is, with the shield 1E, the first joining section 61 and the second joining section 62 are constituted by the exposed portion 46, that is, the remaining portion where the connecting portion 20 that includes the first adhesive 43 is exposed from the liner 45 that covers a portion of the surface side that overlaps with the non-woven mask 2; and the portion on the front surface E1b side of the attachment section E1.

The position of the exposed portion 46 is not particularly limited provided that it is a region on the front surface E1b side of the attachment section E1, and the first side in the width direction of the shield 1E, and the position is set to a position whereby the actions and effects of the dispenser 100 described previously can be advantageously provided. Additionally, the size of the exposed portion 46 is not particularly limited, and is set to a size whereby the actions and effects of the dispenser 100 described previously can be advantageously provided.

In this case, the first joining section 61 and the second joining section 62 are constituted by the exposed portion 46 where the first adhesive 43 is exposed from the liner 45. Here, because the thickness of the adhesive can be reduced, increases in the thicknesses of the first joining section 61 and the second joining section 62 can be suppressed. Additionally, because the first adhesive 43 does not function only as the connecting portion 20, but also functions as the first joining section 61 and the second joining section 62, the configuration of the shield 1 can be simplified.

FIG. 14 is a drawing schematically illustrating a cross-section of a shield 1F used in a dispenser 100 according to a sixth embodiment. As illustrated in FIG. 14, the shield 1F used in the dispenser 100 according to the sixth embodiment differs from the shield 1A used in the dispenser 100 according to the first embodiment in that the connecting portion 20 is formed by a first adhesive 43 instead of the mechanical engagement means including the male engagement elements 31, and a portion on the front surface E1b side of the attachment section E1 is covered by an easy-release layer 47, on the surface side opposite the surface that overlaps with the non-woven mask. That is, with the shield 1F, the first joining section 61 and the second joining section 62 are constituted by the connecting portion 20 that includes the first adhesive 43; and an exposed portion 48, that is, a remaining portion that is not covered by the easy-release layer 47, of the front surface E1b side of the attachment section E1 of which a portion is covered by the easy-release layer 47 on the surface side of the side opposite the surface that overlaps with the non-woven mask 2. Note that an adhesive layer may be interposed between the easy-release layer 47 and the front surface E1b side of the attachment section E1. Additionally, an adhesive layer may be provided on the exposed portion, that is, the remaining portion where the easy-release layer 47 is not provided, on the front surface E1b side of the attachment section E1.

The easy-release layer 47 is provided to reduce the adhesive strength of the adhesive. The easy-release layer 47 is provided by coating a release agent or is formed by performing a known treatment. The release agent is not particularly limited and any type may be used. Examples thereof include waxes, silicone resins, fluororesins, amino alkyd resins, melamine resins, polyester resins, acrylic resins, and inorganic powders. Examples of easy-release treatments include corona discharge treatments, plasma treatments, and vapor deposition treatments.

In this case, adhesive strength between the remaining portion, namely the exposed portion 48, and the connecting portion 20 that includes the first adhesive 43 is stronger than adhesive strength between the easy-release layer 47 and the connecting portion 20 that includes the first adhesive 43. Due to this difference in adhesive strengths, the remaining portion, namely the exposed portion 48, and the connecting portion 20 that includes the first adhesive 43 function as the first joining section 61 and the second joining section 62. Here, because the thickness of the adhesive can be reduced, increases in the thicknesses of the first joining section 61 and the second joining section 62 can be suppressed.

The present invention is not limited to the embodiments described above.

For example, in the embodiments described above, the plurality of shields 1 are mutually detachably joined at the first joining section 61 positioned in the region on the first side in the width direction of the shield 1 and the second joining section 62 positioned in the region on the second side opposite the first side in the width direction of the shield 1. However, the positions at which the plurality of shields 1 are mutually detachably joined are not limited to the positions of the first joining section 61 and the second joining section 62. That is, the plurality of shields 1 may be joined at any position, provided that they are mutually detachably joined. As such, sliding and the like against each other in the container 50 is suppressed and, therefore, sticking of the shields 1 to each other due to the generation of static electricity is suppressed. As a result, the user can easily dispense the shields 1 from the dispensing opening of the container 50.

Additionally, in the embodiments described above, the container 50 includes the dispensing opening 51 that is open between positions, each covering the first joining section 61 and the second joining section 62, in the stacking direction of the stacked body 60. However, it is sufficient that the container 50 include a dispensing opening 51 through which the shields 1 can pass, and a configuration is possible in which the container 50 includes a dispensing opening 51 that is open to a side surface thereof (a surface intersecting the width direction of the shields 1). In this case as well, provided that the plurality of shields 1 are mutually detachably joined at any position, sliding and the like against each other in the container 50 will be suppressed and, therefore, sticking of the shields 1A to each other due to the generation of static electricity will be suppressed. Thus, a user can easily dispense the shields 1 from the dispensing opening of the container 50.

Additionally, in the embodiments described above, the dispensing means are configured as the dispensing opening 51 that is open in the container 50 from the time of distribution of the dispenser 100. However, the dispensing means may be configured such that the dispensing opening 51 is formed at a time of use instead of being open at the time of distribution of the dispenser 100. For example, a configuration is possible in which, at the time of distribution of the dispenser 100, the container 50 includes a cutout portion connected by a score line (e.g. perforation) to a portion corresponding to the dispensing opening 51, and the dispensing opening 51 is formed by the user tearing off this cutout portion at a time of use of the dispenser 100.

The invention claimed is:

1. A dispenser, comprising:
a shield configured to protect eyes of a user wearing a non-woven mask; and
a container configured to house a stacked body constituted of a plurality of the shields stacked in a mutually detachable joined state;
wherein,
the stacked body includes at least a first shield, a second shield, and a third shield, stacked in this order toward one direction of a stacking direction;
the first shield and the second shield are mutually detachably joined at a first joining section positioned in a region on a first side in a width direction of the shield;
the second shield and the third shield are mutually detachably joined at a second joining section positioned in a region on a second side opposite the first side in the width direction of the shield
the container includes dispensing means through which the shields can pass; and further wherein
the second shield is unattached to the first shield at the second side, and the second shield is unattached to the third shield at the second side.

2. The dispenser according to claim 1, wherein:
the container includes the dispensing means located between positions, each covering the first joining section and the second joining section, in the stacking direction in a state in which the stacked body is stored.

3. The dispenser according to claim 2, wherein:
the shield includes an attachment section that is formed on a lower edge section side of the shield, the attachment section comprises:
a connecting portion on a back surface of the attachment section; and
a joining means on a front surface of the attachment section.

4. The dispenser according to claim 3, wherein the connecting portion comprises male engagement elements; and joining means that detachably join with the male engagement elements.

5. The dispenser according to claim 4, wherein the joining means comprises a nonwoven material.

\* \* \* \* \*

UNITED STATES PATENT AND TRADEMARK OFFICE
CERTIFICATE OF CORRECTION

PATENT NO. : 10,532,879 B2
APPLICATION NO. : 15/767072
DATED : January 14, 2020
INVENTOR(S) : Tomomi Kosaki et al.

It is certified that error appears in the above-identified patent and that said Letters Patent is hereby corrected as shown below:

In the Specification

Column 1
Line 9 (Approx.)    Delete "Oct. 16," and insert -- Oct. 15, --, therefor.

In the Claims

Column 19
Line 2    In Claim 5, delete "nonwoven" and insert -- non-woven --, therefor.

Signed and Sealed this
Ninth Day of June, 2020

Andrei Iancu
*Director of the United States Patent and Trademark Office*